(12) United States Patent
Schreiber

(10) Patent No.: US 10,775,037 B2
(45) Date of Patent: Sep. 15, 2020

(54) AIRFLOW-CHANNELING SURGICAL LIGHT SYSTEM AND METHOD

(71) Applicant: SLD Technology, Inc., Portland, OR (US)

(72) Inventor: Kevin Joseph Schreiber, Happy Valley, OR (US)

(73) Assignee: SLD Technology, Inc., Portland, OR (US)

(*) Notice: Subject to any disclaimer, the term of this patent is extended or adjusted under 35 U.S.C. 154(b) by 44 days.

(21) Appl. No.: 15/899,031

(22) Filed: Feb. 19, 2018

(65) Prior Publication Data

US 2018/0172258 A1 Jun. 21, 2018

Related U.S. Application Data

(63) Continuation-in-part of application No. 14/877,762, filed on Oct. 7, 2015, now Pat. No. 9,895,202, which
(Continued)

(51) Int. Cl.
*F21V 29/61* (2015.01)
*A61B 90/30* (2016.01)
(Continued)

(52) U.S. Cl.
CPC .............. *F21V 29/61* (2015.01); *A61B 90/30* (2016.02); *A61L 9/00* (2013.01); *A61L 9/16* (2013.01);
(Continued)

(58) Field of Classification Search
CPC .... F21V 29/61; F21V 29/677; F21V 33/0088; A61B 90/30; A61B 2034/2048; A61B 2090/309; A61L 9/00; A61L 9/16; A61L 9/205; A61L 9/22; A61L 2209/11; A61L 2209/12; A61L 2209/14; F21W 2131/205
See application file for complete search history.

(56) References Cited

U.S. PATENT DOCUMENTS 2,449,362 A 9/1948 Bell et al.
2,962,582 A 11/1960 Croft
(Continued)

FOREIGN PATENT DOCUMENTS

DE 3331299 3/1985
EP 2679213 1/2014
(Continued)

OTHER PUBLICATIONS

Copenheaver, "International Search Reported", International Publication No. 2016/040706, dated Dec. 10, 2015, 2 pages.

*Primary Examiner* — Bao Q Truong

(57) ABSTRACT

A light system includes a main body defining an internal chamber and a lighting assembly secured to the main body, wherein the lighting assembly comprises at least one light unit configured to emit light. The light system further includes a fan configured to generate an airflow and an airflow circuit configured to direct the airflow out of the main body of the lighting assembly. The light system also includes a tilt detection unit configured to detect a tilt angle of the lighting assembly and to generate a control signal to cause a speed of the airflow generated by the fan to change based at least on a detected change in the tilt angle of the lighting assembly.

20 Claims, 10 Drawing Sheets

Related U.S. Application Data is a continuation-in-part of application No. 14/789,338, filed on Jul. 1, 2015, now Pat. No. 9,671,100.

(51) Int. Cl.

| | | |
|---|---|---|
| *F21V 29/67* | (2015.01) | |
| *A61L 9/00* | (2006.01) | |
| *F21V 33/00* | (2006.01) | |
| *A61L 9/16* | (2006.01) | |
| *A61L 9/20* | (2006.01) | |
| *A61L 9/22* | (2006.01) | |
| *F21W 131/205* | (2006.01) | |
| *A61B 34/20* | (2016.01) | |

(52) U.S. Cl.
CPC ............... *A61L 9/205* (2013.01); *A61L 9/22* (2013.01); *F21V 29/677* (2015.01); *F21V 33/0088* (2013.01); *A61B 2034/2048* (2016.02); *A61B 2090/309* (2016.02); *A61L 2209/11* (2013.01); *A61L 2209/12* (2013.01); *A61L 2209/14* (2013.01); *F21W 2131/205* (2013.01)

(56) References Cited

U.S. PATENT DOCUMENTS

| | | | |
|---|---|---|---|
| 3,792,230 A | 2/1974 | Ray | |
| 3,864,547 A | 2/1975 | Ray | |
| 4,356,535 A | 10/1982 | Chu | |
| 4,630,182 A | 12/1986 | Moroi et al. | |
| 6,244,720 B1 | 6/2001 | Neff | |
| 7,144,140 B2 | 12/2006 | Sun et al. | |
| 7,682,054 B2 | 3/2010 | Hsu et al. | |
| 8,226,273 B2 | 7/2012 | Lai | |
| 8,319,408 B1* | 11/2012 | Horng | F21V 3/00 313/46 |
| 2002/0195953 A1* | 12/2002 | Belliveau | H05B 41/2928 315/149 |
| 2003/0141050 A1* | 7/2003 | Brocksopp | F01P 3/18 165/299 |
| 2007/0236668 A1* | 10/2007 | Suzuki | G03B 21/16 353/57 |
| 2013/0223078 A1* | 8/2013 | Quadri | F21V 9/04 362/294 |
| 2013/0344795 A1 | 12/2013 | Schreiber | |
| 2014/0293622 A1 | 10/2014 | Hauschulte | |
| 2016/0040866 A1* | 2/2016 | Quadri | F21V 29/67 362/373 |

FOREIGN PATENT DOCUMENTS

| | | |
|---|---|---|
| FR | 2032919 | 11/1970 |
| GB | 864894 | 4/1961 |

\* cited by examiner

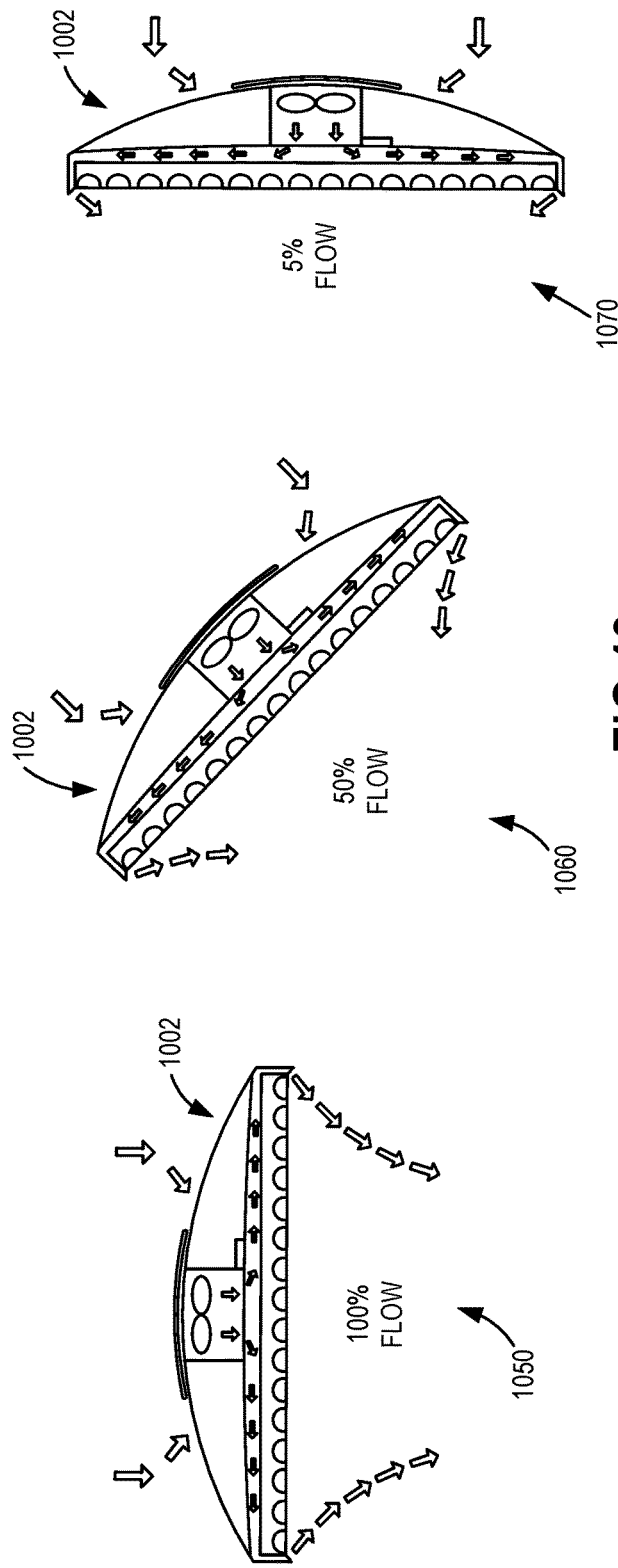
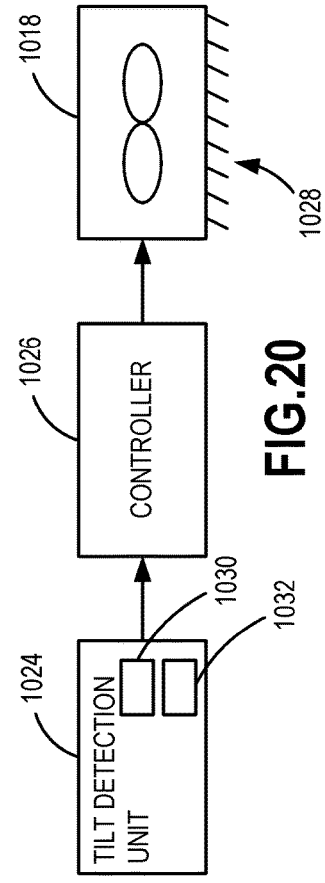
FIG.19
FIG.20

| TABLE 1 | |
|---|---|
| ANGLE | AIRFLOW |
| ⋮ | ⋮ |

| TABLE 2 | |
|---|---|
| ANGLE | AIRFLOW |
| ⋮ | ⋮ |

| TABLE 3 | |
|---|---|
| ANGLE | AIRFLOW |
| ⋮ | ⋮ |

AIRFLOW-CHANNELING SURGICAL LIGHT SYSTEM AND METHOD

CROSS-REFERENCE TO RELATED APPLICATIONS

This is a Continuation-in-Part of application Ser. No. 14/877,762, filed Oct. 7, 2015, which is a Continuation-in-Part of application Ser. No. 14/789,338 filed Jul. 1, 2015, now U.S. Pat. No. 9,671,100. The disclosures of the prior applications are hereby incorporated by reference herein in their entirety.

FIELD OF THE DISCLOSURE

Embodiments of the present disclosure generally relate to an airflow-channeling light system and method, such as may be used within a surgical operating room.

BACKGROUND OF THE DISCLOSURE

Hospital operating rooms typically include a surgical light that is positioned over a surgical site. The surgical light contains one or more light sources that are configured to emit a focused beam of light directly onto a surgical target zone.

Additionally, a supply air array is positioned within a ceiling directly above the surgical light and the surgical site target zone. The supply air array includes vents through which filtered air is supplied and directed toward the surgical site. The vents may include filters to filter the air that passes therethrough. Sidewall vents return contaminated air from the perimeter of the room to an air filtration system positioned upstream of the supply air array. The air filtration system supplies filtered air to the room through the supply air array with unidirectional, downward airflow.

Because the surgical light may be positioned directly over the surgical target zone, the surgical light may block airflow generated by the supply air array and create a low pressure zone underneath the surgical light. The low pressure zone causes air turbulence underneath the surgical light. Due to turbulent airflow, various contaminants generated through a surgical procedure may be circulated within the surgical environment. For example, surgical staff may carry particulate and bacterial contaminants that may be dispersed directly above a surgical site in the absence of filtered, downward, unidirectional flow. Further, bone fragments, biological fluids, and blood may be projected upward toward the surgical light head, which is cleaned and sterilized between surgical procedures.

Accordingly, a need exists for a system and method of providing uninterrupted, reduced turbulence airflow underneath a surgical light. A need exists for a system and method that reduce the possibility of contaminants being dispersed over and within a surgical site.

SUMMARY OF THE DISCLOSURE

Certain embodiments of the present disclosure provide a light system that includes a main body defining an internal chamber and a lighting assembly secured to the main body, wherein the lighting assembly comprises at least one light unit configured to emit light. The light system further includes a fan configured to generate an airflow and an airflow circuit configured to direct the airflow out of the main body of the lighting assembly. The light system also includes a tilt detection unit configured to detect a tilt angle of the lighting assembly and to generate a control signal to cause a speed of the airflow generated by the fan to change based at least on a detected change in the tilt angle of the lighting assembly.

Certain embodiments of the present disclosure provide a method for controlling airflow from a lighting assembly that includes detecting a tilt angle of a lighting assembly, wherein the lighting assembly includes at least one light unit configured to emit light and an airflow circuit configured to direct the airflow from a fan out of the main body of the lighting assembly. The method further includes generating a control signal to cause a speed of airflow generated by the fan to change based at least on the detected change in the tilt angle of the lighting assembly.

Certain embodiments of the present disclosure provide one or more computer storage media having computer-executable instructions for controlling airflow from a lighting assembly that, upon execution by a processor, cause the processor to at least detect a tilt angle of a lighting assembly, wherein the lighting assembly comprises at least one light unit configured to emit light and an airflow circuit configured to direct the airflow from a fan out of the main body of the lighting assembly. The one or more computer storage media having computer-executable instructions for controlling airflow from a lighting assembly that, upon execution by a processor, cause the processor to at least generate a control signal to cause a speed of airflow generated by the fan to change based at least on the detected change in the tilt angle of the lighting assembly.

BRIEF DESCRIPTION OF THE DRAWINGS

FIG. 19 illustrates operation of the airflow-channeling surgical light system of FIG. 18.

FIG. 20 is a block diagram of a control arrangement, according to an embodiment of the present disclosure.

FIG. 21 illustrates control tables, according to an embodiment of the present disclosure.

DETAILED DESCRIPTION OF THE DISCLOSURE

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Certain embodiments of the present disclosure provide an airflow-channeling surgical light system that may include an airflow circuit having one or more air paths that are configured to channel filtered air to a periphery or outer perimeter of a lighting assembly. The system is configured to deliver air directly under the lighting assembly. In at least one embodiment, the system may include a quick connect perimeter protective insert that includes a plurality of air passages. The positioning of the air passages prevents contaminants from easily entering the air path(s) and allows the perimeter protective insert to easily be removed for cleaning. The perimeter protective insert may also include a protective shield to lend additional support to the insert and also to help protect a light lens of the lighting assembly from contamination.

Figure 1:
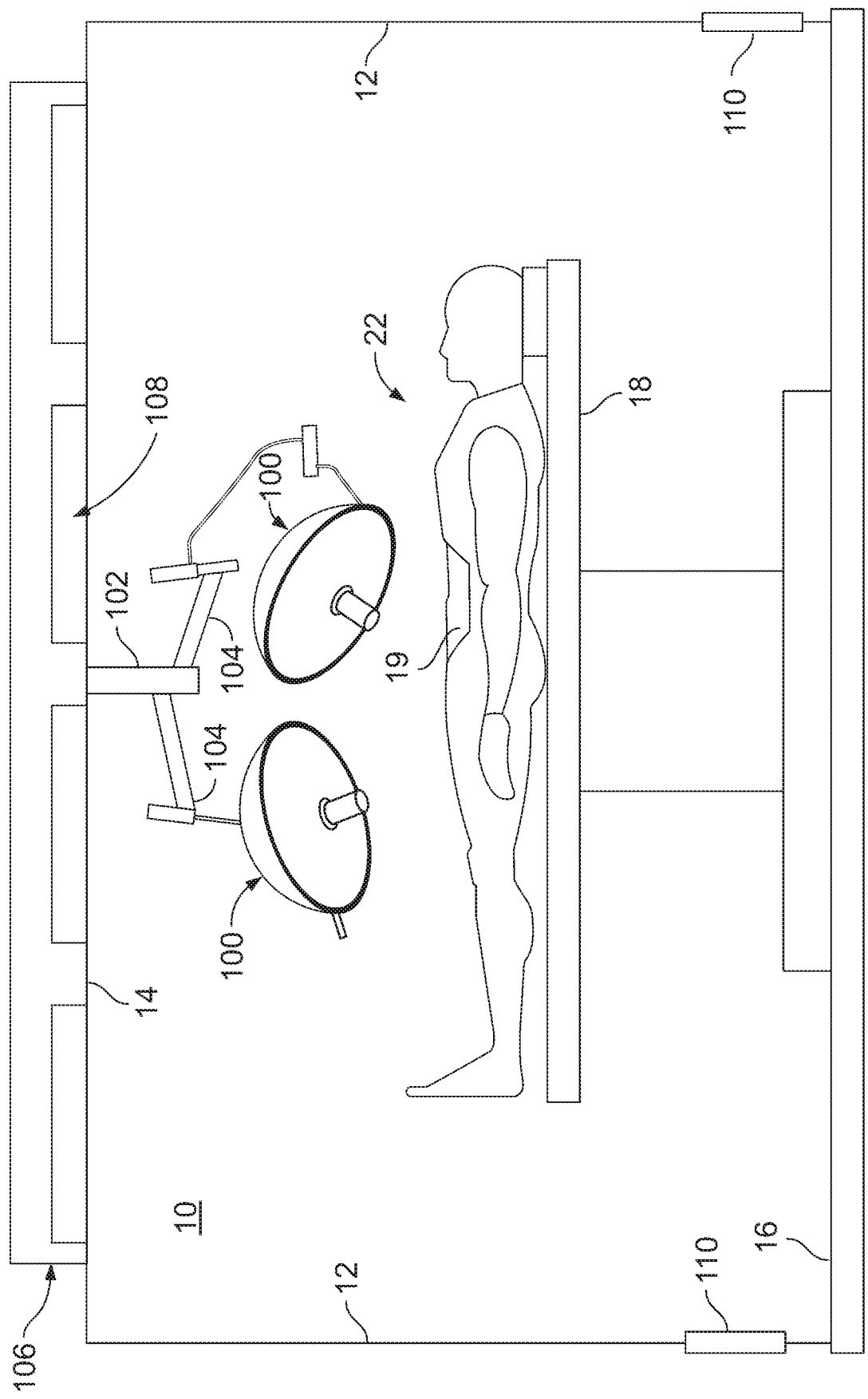
FIG. 1 illustrates a lateral view of an operating room, according to an embodiment of the present disclosure.

FIG. 1 illustrates a lateral view of an operating room 10, according to an embodiment of the present disclosure. The operating room 10 may be defined by walls 12, a ceiling 14, and a floor 16. An operating table 18 may be supported on the floor 16. The operating table 18 may include a support bed 20 that is configured to support a patient 22. A surgical site 19 may be located on the patient 22.

An airflow-channeling surgical light system 100 is suspended from the ceiling 14 above the operating table 18, which may define a sterile field. A support beam 102 extends downwardly from the ceiling 14. One or more boom arms 104 may extend from the support beam 102. The airflow-channeling surgical light system 100 connects to a boom arm 104. As shown in FIG. 1, two surgical light assemblies 100 may be coupled to two separate and distinct boom arms 104. Alternatively, more or less surgical light assemblies 100 than shown may be used.

A supply air array 106 may be secured above the ceiling 104, such as within a plenum. The supply air array 106 is configured to direct airflow into the operating room 10. The supply air array 106 may include one or more air diffusers 108 that are connected to one or more return vents 110, which may be secured to one or more walls 12. For example, the supply air array 106 directs airflow into the operating room through the diffusers 108. The airflow passes into the return vents 110, which channel the airflow back into the supply air array 106, where the airflow is filtered and directed back into the operating room through the air diffusers 108.

Figure 2:
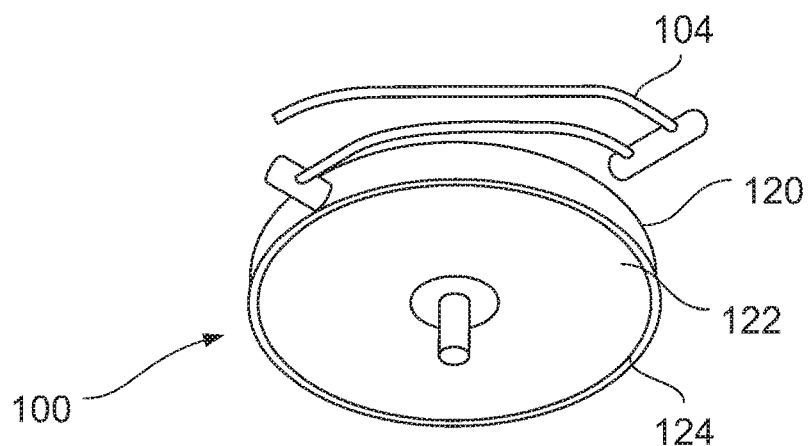
FIG. 2 illustrates a perspective bottom view of an airflow-channeling surgical light system, according to an embodiment of the present disclosure.

FIG. 2 illustrates a perspective bottom view of the airflow-channeling surgical light system 100, according to an embodiment of the present disclosure. The surgical light system 100 may include a main body 120 that is configured to couple to the boom arm 104. A lighting assembly 122 is secured to the main body 120 and may include one or more light units that are configured to direct light through the sterile field onto the surgical site 19. For example, the light units may be or include a plurality of light emitting diodes (LEDs). Optionally, the light units may be incandescent light bulbs, fluorescent light bulbs, halogen light bulbs, and/or the like.

An airflow outlet 124 is formed around the periphery of the lighting assembly 122. The periphery is the outer perimeter portion of the lighting assembly 122. An airflow circuit, including the airflow outlet 124, may also extend around other portions of the lighting assembly 122, such as top and bottom portions of the lighting assembly 122, as described below. The airflow outlet 124 is configured to direct airflow underneath the lighting assembly 122. The airflow outlet 124 does not extend through the lighting assembly 122. In at least one embodiment, an entire airflow circuit, which may include the airflow outlet 124, does not extend into or through the lighting assembly 122. Instead, the airflow circuit and outlet 124 extend around an outer perimeter or periphery of the lighting assembly 122. That is, the airflow circuit is routed around the lighting assembly 122 so as not to interfere with operation of the lighting assembly 122. A protective insert may be configured to be removably secured to the main body, such as to the airflow outlet 124.

Figure 3:
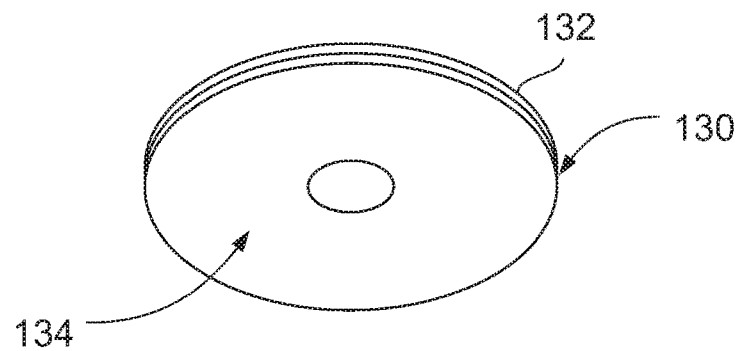
FIG. 3 illustrates a perspective bottom view of a protective insert, according to an embodiment of the present disclosure.

FIG. 3 illustrates a perspective bottom view of a protective insert 130, according to an embodiment of the present disclosure. The protective insert 130 may include a support frame 132 that is configured to be removably secured to and/or within the airflow outlet 124, such as within a retaining channel of a peripheral airflow channel. For example, the support frame 132 may be configured to snapably, latchably, or otherwise removably couple to the airflow outlet 124. In at least one embodiment, the support frame 132 may be configured to be secured within the airflow outlet 124 through an interference fit, a press fit, and/or the like.

The support frame 132 may include a plurality of air passages that are configured to receive airflow from the airflow outlet 124 and direct the airflow underneath the lighting assembly 122 (shown in FIG. 2). As shown, the support frame 132 may be shaped as a ring. Optionally, the support frame 132 may be formed as various other shapes and sizes, depending on the shape and size of the surgical light system 100.

The protective insert 130 may also include a transparent shield 134 that extends between interior edges of the support frame 132. The transparent shield 134 may be formed of glass, clear plastic, and/or the like. Optionally, the transparent shield 134 may be tinted. The transparent shield 134 is configured to extend beneath a lens and/or lower transparent surface of the lighting assembly 122. In this manner, the transparent shield 134 is configured to protect the lighting assembly 122 from contaminants. Alternatively, the protective insert 130 may not include the transparent shield 134.

In operation, the support frame 132 of the protective insert 130 is configured to provide a circuitous airflow path between the airflow outlet 124 and a volume beneath the surgical light system 100. As such, the support frame 132 reduces the possibility that contaminants (such as bacteria, bodily fluids, and the like) enter the airflow outlet 124. Further, the transparent shield 134 protects the lighting assembly 122 from contaminants. After a surgical operation, the protective insert 130 may be removed from the surgical light system 100 and cleaned in order to remove any contaminants thereon or therein.

Alternatively, the support frame 132 may be permanently fixed to the main body 120. For example, the support frame 132 may be permanently fixed to or otherwise within the airflow outlet 124.

Figure 4:
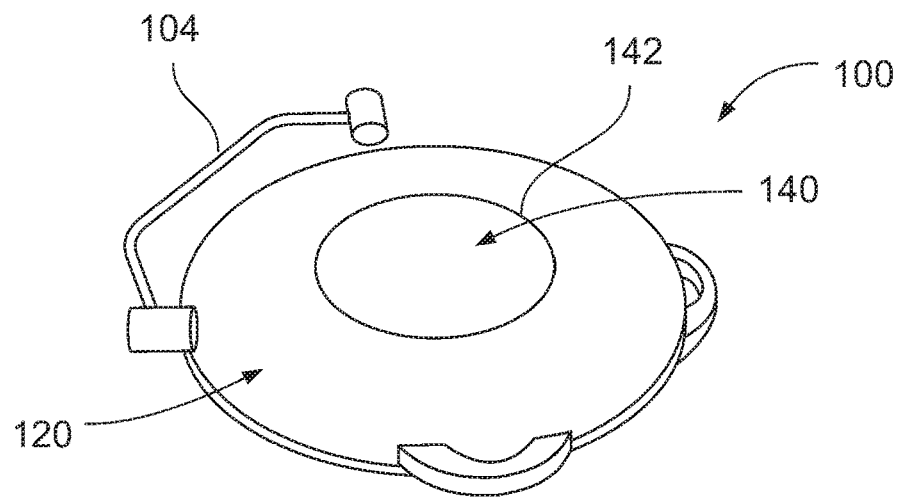
FIG. 4 illustrates a perspective top view of an airflow-channeling surgical light system, according to an embodiment of the present disclosure.

FIG. 4 illustrates a perspective top view of the airflow-channeling surgical light system 100, according to an embodiment of the present disclosure. A covering cap 140, such as a dome, may be secured over a portion of the main body 120. An air inlet passage 142 may be defined between a lower surface of the covering cap 140 and an upper surface of the main body 120. In operation, airflow is drawn into the main body 120 through the air inlet passage 142. The airflow is channeled from the air inlet passage 142 to an internal airflow circuit (such as formed by one or more conduits, pipes, passages, and/or the like), which channels the airflow around the lighting assembly 122 (shown in FIG. 2) and out of the system 100 by way of the airflow outlet 124 (shown in FIG. 2).

Figure 5:
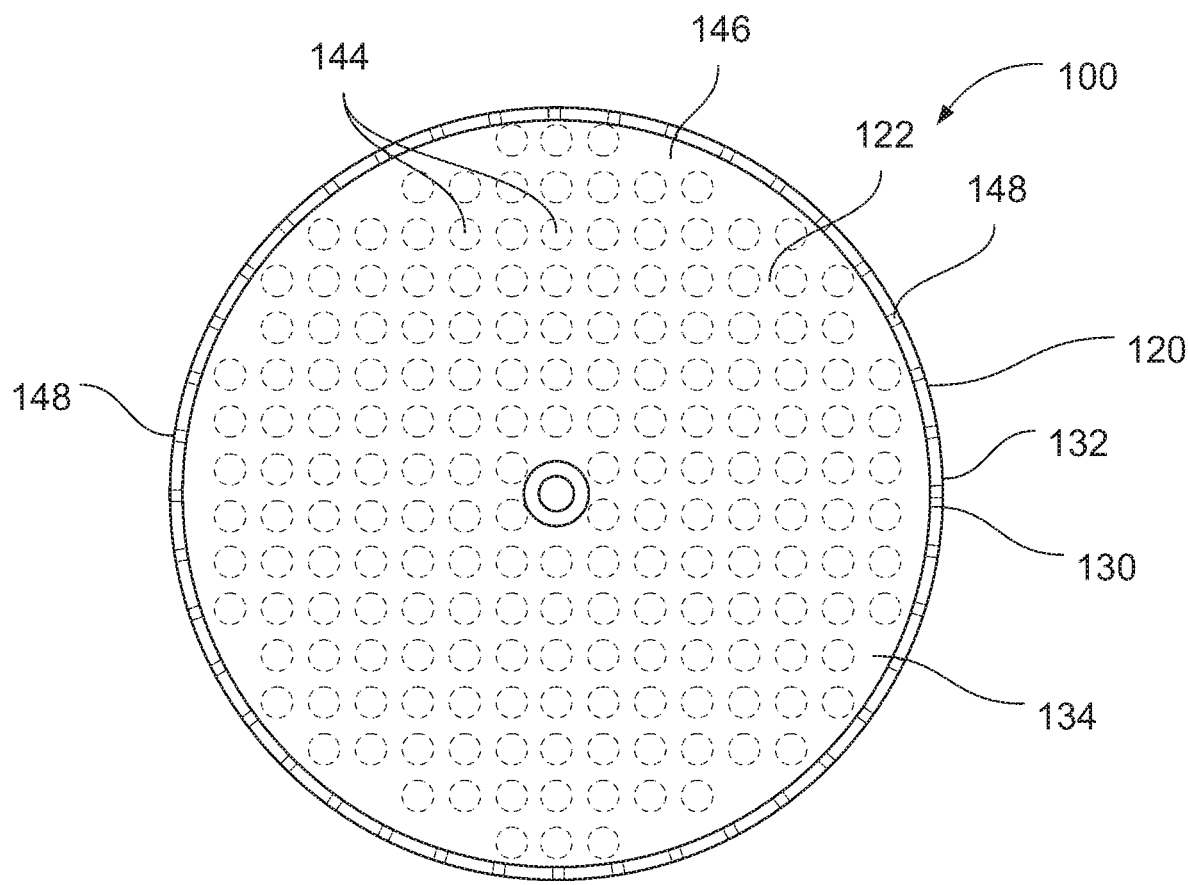
FIG. 5 illustrates a bottom view of an airflow-channeling surgical light system, according to an embodiment of the present disclosure.

FIG. 5 illustrates a bottom view of the airflow-channeling surgical light system 100, according to an embodiment of the present disclosure. The lighting assembly 122 may include a plurality of light units 144 above a lens or transparent panel 146. The transparent shield 134 of the protective ring 130 is disposed underneath the lens or transparent panel 146.

The support frame 132 of the protective insert 130 is secured within the airflow outlet 124. As noted, the airflow outlet 124 extends around a periphery of the lighting assembly 122. The support frame 132 may include a plurality of air outlet passages 148. The air outlet passages 148 may be disposed at a common level. Optionally, one or more air outlet passages 148 may be disposed at different levels than one or more other air outlet passages 148.

Figure 6:
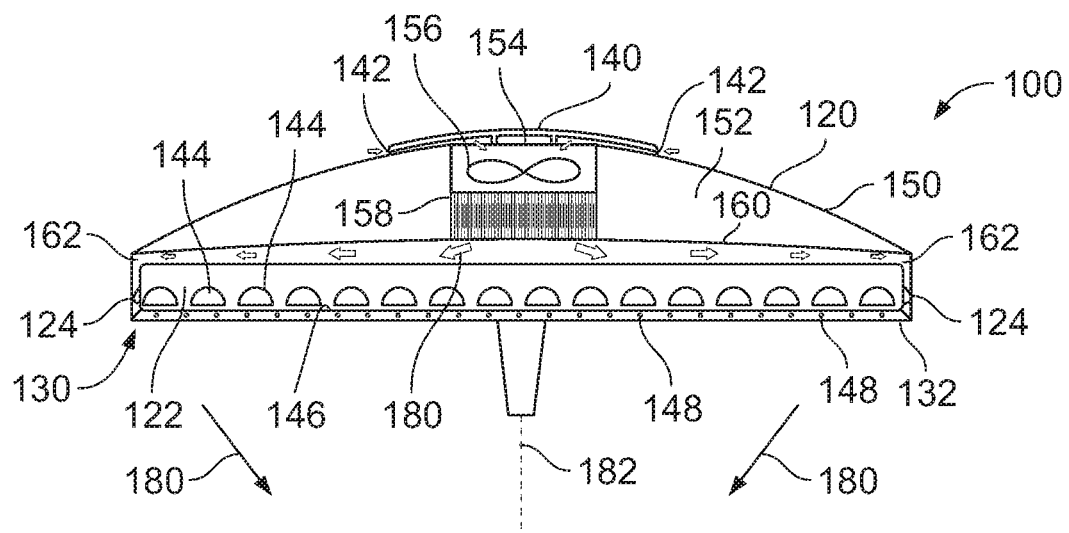
FIG. 6 illustrates a lateral internal view of an airflow-channeling surgical light system, according to an embodiment of the present disclosure.

FIG. 6 illustrates a lateral internal view of the airflow-channeling surgical light system 100, according to an embodiment of the present disclosure. The main body 120 may include an outer shroud 150 that defines an internal chamber 152. An opening 154 is formed through a top of the outer shroud 150. The covering cap 140 is secured to the main body 120 within the opening 154 such that the air inlet passage 142 forms (or otherwise is) a gap between a lower surface of the covering cap 140 and an upper surface of the outer shroud 150.

A fan 156 (such as an electric, piezoelectric, or other such fan) is secured within the internal chamber 152 underneath the covering cap 140. An air filter 158, such as a high-efficiency particulate arrestance (HEPA) filter, may be positioned underneath the fan 156. However, any air filtering device may be used, for example, any type of air filtering device that captures and/or contains contaminants, such as any device used to filter, trap or capture bacteria, viruses, mold, fungi, allergens, volatile organic compounds (VOCs), etc. Thus, in some embodiments, instead of a HEPA filter, an ultra low penetration air (ULPA) filter or an electrostatic filter may be used, among others.

An upper air channel 160 is secured above the lighting assembly 122. The upper air channel 160 may not extend into the lighting assembly 122. Instead, the upper air channel 160 provides an air conduit that extends over the lighting assembly 122. The upper air channel 160 connects to one or more lateral or peripheral air channels 162 that extend around a periphery of the lighting assembly 122. The airflow outlet 124 connects to the peripheral air channel 162. For example, the airflow outlet 124 may form a terminal end of the peripheral air channel 162. The airflow outlet 124 connects to the support frame 132 of the protective insert 130. Accordingly, an airflow circuit extends from the air inlet passage 142 through the fan 156 and the air filter 158. The airflow circuit continues from the fan 156 and the air filter 158 into the upper air channel 160, which connects to the peripheral air channel 162, and into the airflow outlet 124, which connects to the support frame 132, which includes the air outlet passages 148. Accordingly, the airflow circuit extends around the lighting assembly 122, and may not extend into the lighting assembly 122.

The upper air channel 160 may be one or more linear channels formed above the lighting assembly 122. Optionally, the upper air channel 160 may be an internal cavity that forms a disc shape within the main body 120. The peripheral air channels 162 may include one or more channels connecting to the upper air channel 160. For example, a single circumferential air channel 162 may circumferentially extend from the upper air channel 160.

As shown, flowing air (that is, airflow) enters the surgical light system 100 through the air inlet passage 142 and is directed out through the air outlet passages 148. The fan 156 is downstream from the air inlet passage 142. The air filter 158 is downstream from the fan 156. The upper air channel 160 is downstream from the air filter 158. The peripheral air channel 162 is downstream from the upper air channel 160. The airflow outlet 124 is downstream from the peripheral air channel 162 (or otherwise forms a downstream terminal portion of the peripheral air channel 162). The air outlet passages 148 of the protective insert 130 are downstream from the airflow outlet 124.

In operation, as the fan 156 is activated, the rotation of fan 156 draws in air outside of the surgical light system 100 through the air inlet passage 142. The fan 156 moves the air through the air filter 158, which filters contaminants from the air. The fan 156 continues to move the air through the air filter 158 and into the upper air channel 160. The air 180 is then channeled to the peripheral air channel 162 and out through the airflow outlet 124. The air 180 then passes through a circuitous air path within the support frame 132 and out through the air outlet passages 148. The air outlet passages 148 may be angled to shunt and direct the air 180 out of the system 100 at an angle towards a central imaginary axis 182 extending downwardly from a center of the lighting assembly 122. The axis 182 is "imaginary" in that it is a virtual axis that extends through and out of the lighting assembly 122.

The circuitous air path includes one or more turns that re-direct the airflow therein. For example, the turn(s) may cause the airflow to turn at a right angle. As another example, the turn(s) may cause the airflow to turn in an opposite direction from a previous direction of travel (for example, in a direction that is 180 degrees from the initial direction of travel).

Figure 7:
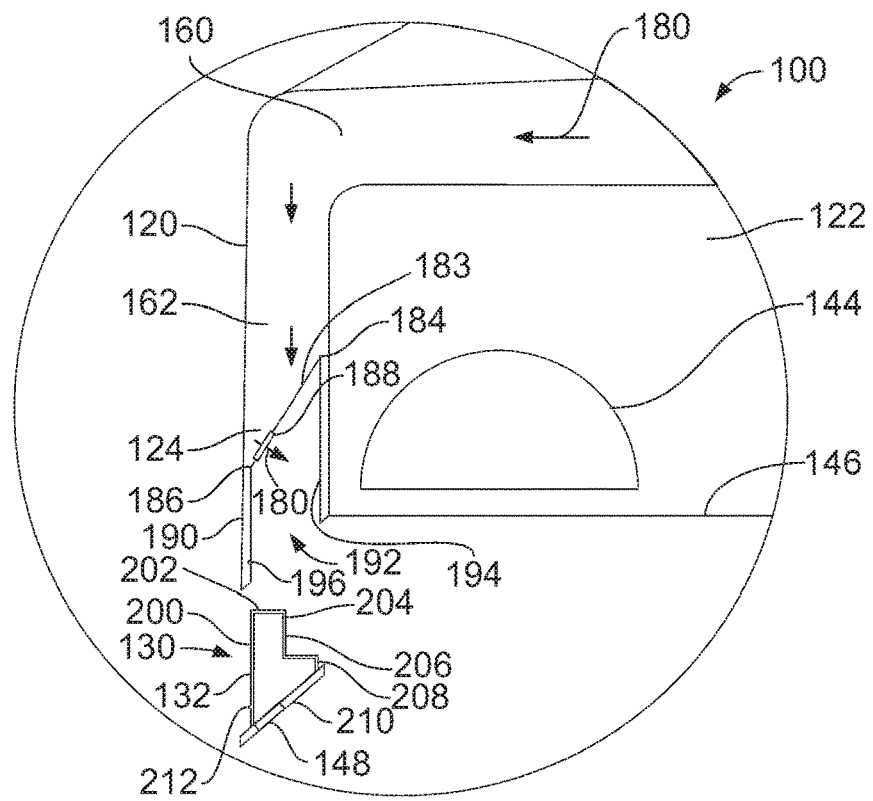
FIG. 7 illustrates a cross-sectional view of a support frame of a protective insert removed from an airflow outlet of an airflow-channeling lighting system, according to an embodiment of the present disclosure.

FIG. 7 illustrates a cross-sectional view of the support frame 132 of the protective insert 130 removed from the airflow outlet 124 of the airflow-channeling lighting system 100, according to an embodiment of the present disclosure. As shown, the airflow outlet 124 may be formed by an angled wall 183 that angles downwardly from an inboard area 184 (that is, closer to the central imaginary axis 182) to an outboard area 186 (that is, further from the central imaginary axis 182). An opening 188 is formed through the angled wall 183. The opening 188 allows air 180 to pass therethrough in a direction that is angled toward the central imaginary axis 182 (shown in FIG. 6).

The main body 120 may include a lower rim 190 that extends below the airflow outlet 124. A retaining channel 192 may be defined between an outer peripheral portion 194 of the lighting assembly 122 and the lower rim 190. The lower rim 190 may include a circumferential retaining divot 196.

The support frame 132 includes an outboard wall 200 that connects to an upper rim 202, which, in turn, connects to an inboard wall 204 having an opening 206 formed therethrough. The inboard wall 204 may connect to a support wall 208 that connects to an angled wall 210 having the air outlet passages 148 formed therethrough. A detent 212 (such as a ridge, lip, or other such protuberance) extends radially outward from the outboard wall 200 and is configured to be securely retained within the retaining divot 196. In this manner, the support frame 132 may be removably secured to the main body 120. Alternatively, the lower rim 190 may include the detent, while the support frame 132 includes retaining divot.

Figure 8:
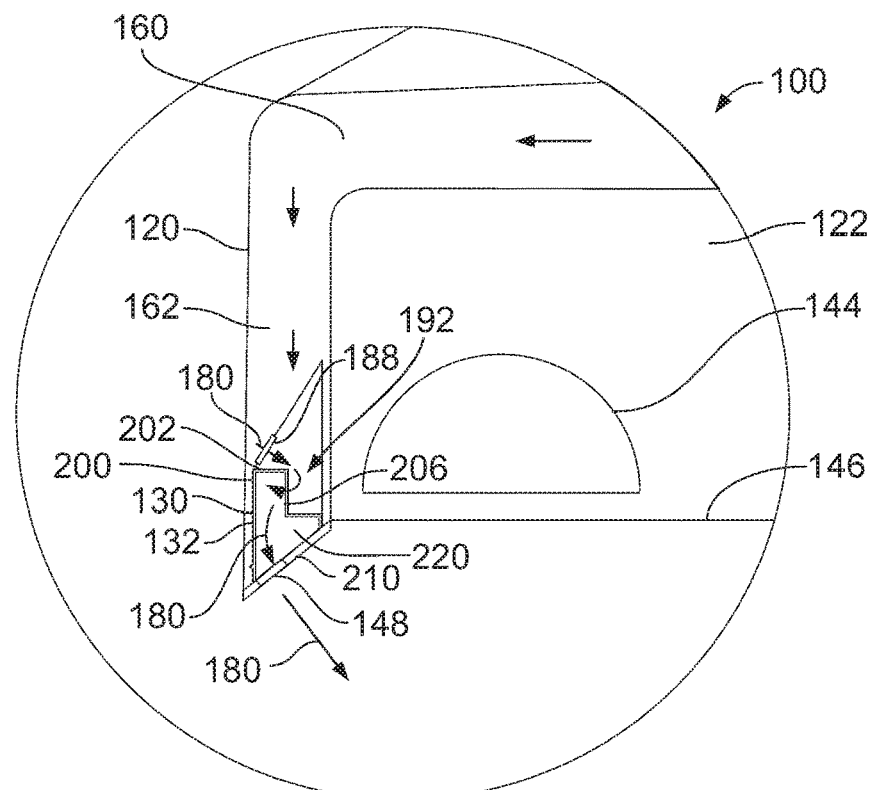
FIG. 8 illustrates a cross-sectional view of a support frame of a protective insert secured within a retaining channel that is in fluid communication with an airflow outlet of an airflow-channeling lighting system, according to an embodiment of the present disclosure.

FIG. 8 illustrates a cross-sectional view of the support frame 132 of the protective insert 130 secured within the retaining channel 192 that is in fluid communication with the airflow outlet 124 of the airflow-channeling lighting system 100, according to an embodiment of the present disclosure. The support frame 132 defines an internal air path 220 therein. The air path 220 extends from the opening 206 to the air outlet passages 148. As shown, air 180 passes out of the opening 180 of the airflow outlet 124 at an angle. The air 180 winds or otherwise turns around the upper rim 202 and enters air path 220 through the opening 206. The air 180 then passes out of the airflow outlet 180 through the air passages 148 at an angle defined by the angled surface of the angled wall 210. As shown, the air 180 is directed out of the support frame 132 at an angle toward the central imaginary axis 182 (shown in FIG. 6). As such, the airflow is directed underneath the lighting assembly 122.

A circuitous air path is formed between the airflow outlet 124 and the air outlet passages 148. The air 180 passes out of the air flow outlet 124 toward the central imaginary axis 182, but is shunted to double-back toward the outboard wall 200 of the support frame 132. The air 180 is then re-directed toward the central imaginary axis 182 by way of the air outlet passages 148 formed through the angled wall 210. The circuitous air path reduces the possibility that contaminants may pass into the peripheral channel 162, as there are structures (for example, the upper rim 202) that shield the opening 188 of the airflow passage 124 from being directly exposed to the surgical site 19 or any contaminants or debris within the sterile field or the room 10.

Referring to FIGS. 1-8, the surgical light system 100 forces air around a periphery of the lighting assembly 120 and out through the air outlet passages 148 of the protective insert 130. The forced air is directed underneath the lighting assembly 120. The delivery of the forced air underneath the lighting assembly 122 generates a pressure zone underneath the lighting assembly 122, which reduces air turbulence, thereby reducing the possibility of contaminants passing onto or into the surgical site 19 or back into the surgical light system 100.

The fan 156 and filter 158 may be interchangeably positioned within the internal chamber 152. The surgical light system 100 may be formed as various other shapes and sizes than shown. For shapes that are not round or symmetrical, a higher concentration of air openings 188 and/or air outlet passages 148 may be disposed along shorter lengths of the system 100 to balance the airflow with the longer sides.

Alternatively, the system 100 may not include the fan and/or the filter. Instead, the system 100 may be coupled to a separate, distinct, and remote air delivery source that is configured to move air through the airflow circuit.

As shown and described, the system 100 is configured to direct pressurized air underneath an entire lower surface of the lighting assembly 122 without blocking any light that is generated by the lighting assembly. Further, because the air is channeled around the lighting assembly (instead of through the lighting assembly), the density of light units within the lighting assembly may be maintained (instead of spreading light units apart to allow for air channels to be formed therebetween). The pressurized air underneath the lighting assembly 122 reduces turbulent recirculation of contaminants directly over the patient and surgical site. The protective insert 130 reduces the likelihood of blood, bone fragments, bodily fluids, or other contaminants from infiltrating into the airflow circuit. The protective ring 130 may be removed from the system 100 after a procedure to be cleaned.

Embodiments may be used in relation to a hospital operating room environment. Optionally, embodiments of the present disclosure may be used in various other settings in which pressurized airflow is to be directed underneath a lighting assembly. For example, embodiments of the present disclosure may be used in dental offices, manufacturing clean rooms, residential spaces, and the like.

Figure 9:
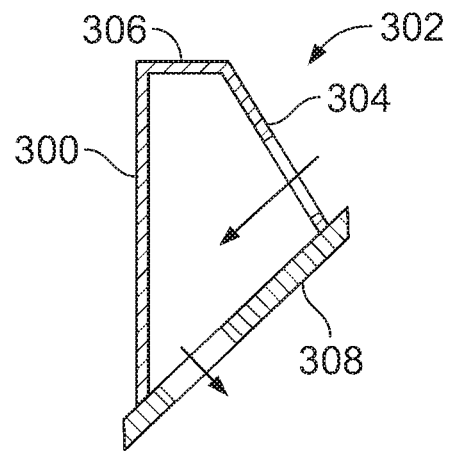
FIG. 9 illustrates a cross-sectional view of a support frame of a protective insert, according to an embodiment of the present disclosure.

FIG. 9 illustrates a cross-sectional view of a support frame 300 of a protective insert 302, according to an embodiment of the present disclosure. The support frame 300 is similar to the support frame 132, except that a single linear wall 304 extends from the upper rim 306 to the angled wall 308. The support frame 300 may be sized and shaped differently than shown. For example, a curved airflow path may be formed through therethrough. The support frame 300 may be used with any of the embodiments of the present disclosure.

Figure 10:
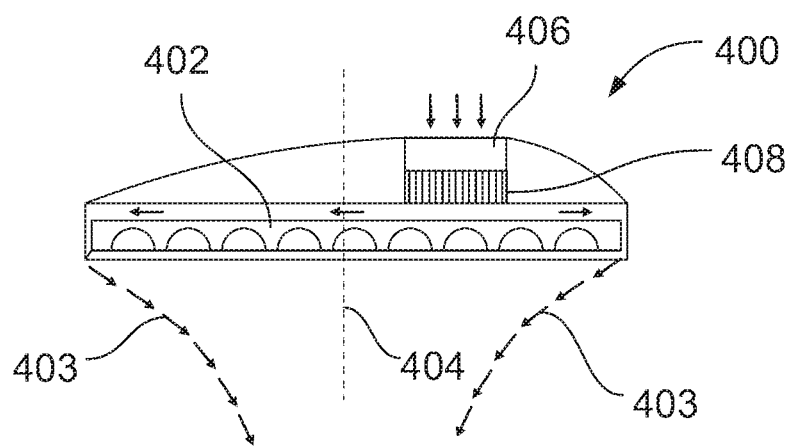
FIG. 10 illustrates a lateral internal view of an airflow-channeling surgical light system, according to an embodiment of the present disclosure.

FIG. 10 illustrates a lateral internal view of an airflow-channeling surgical light system 400, according to an embodiment of the present disclosure. The system 400 is similar to the system 100 and is configured to direct airflow 403 outwardly around a periphery of a lighting assembly 402 at an angle toward a central imaginary axis 404 of the system 400. The system 400 includes a fan 406 and an air filter 408 that may be offset from the central imaginary axis 404. The position of the fan 406 and the air filter 408 as shown in FIG. 10 may be used with respect to any of the embodiments of the present disclosure.

Figure 11:
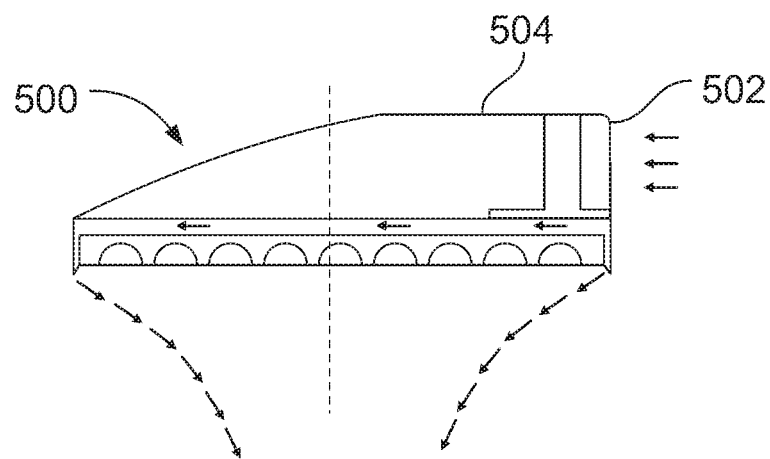
FIG. 11 illustrates a lateral internal view of an airflow-channeling surgical light system, according to an embodiment of the present disclosure.

FIG. 11 illustrates a lateral internal view of an airflow-channeling surgical light system 500, according to an embodiment of the present disclosure. In this embodiment, air inlet passages 502 may be formed through a side (instead of a top) of a main body 504. The air inlet passages 502 as shown in FIG. 11 may be used with respect to any of the embodiments of the present disclosure.

Figure 12:
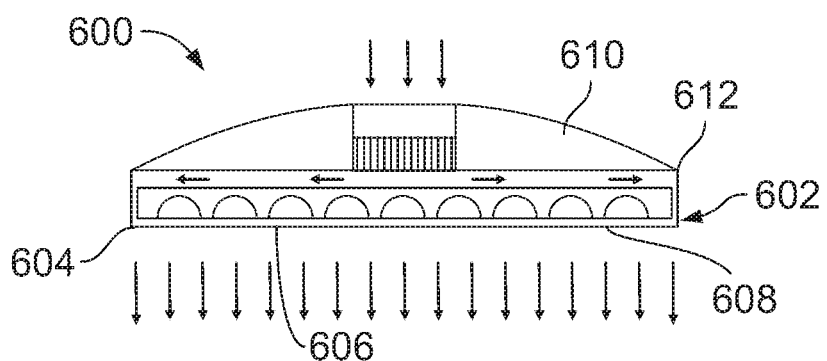
FIG. 12 illustrates a lateral internal view of an airflow-channeling surgical light system, according to an embodiment of the present disclosure.

FIG. 12 illustrates a lateral internal view of an airflow-channeling surgical light system 600, according to an embodiment of the present disclosure. The system 600 may include a protective insert 602 having a support frame 604 connected to a transparent shield 606. An air chamber 608 may be defined between a lens or transparent panel 610 of the lighting assembly 612 and the transparent shield 606. A plurality of air passages may be formed through the transparent shield 606. As such, air may be directed into the air chamber 608 and forced through the air passages underneath the lighting assembly 612.

Figure 13:
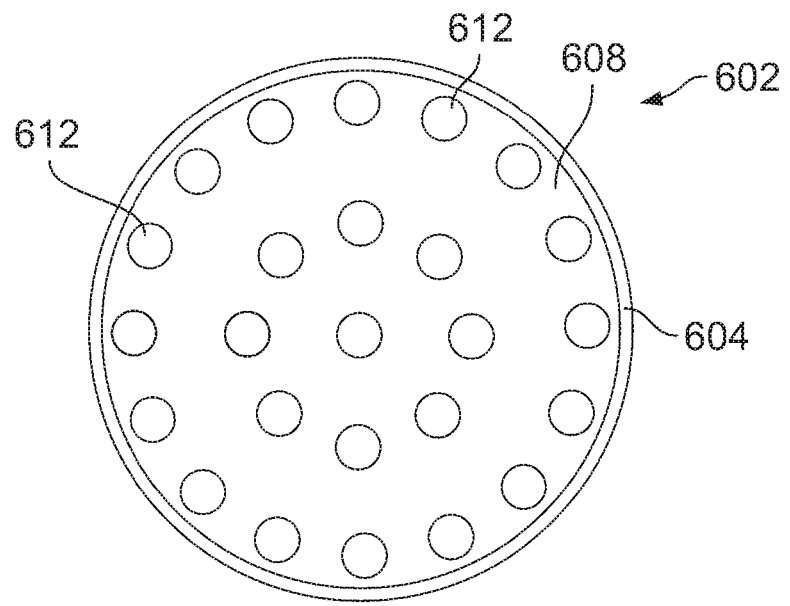
FIG. 13 illustrates a bottom view of a protective insert, according to an embodiment of the present disclosure.

FIG. 13 illustrates a bottom view of the protective insert 602, according to an embodiment of the present disclosure. As shown, a plurality of air passages 612 are formed through the transparent shield 606. The protective insert 602 shown and described with respect to FIGS. 12 and 13 may be used with any of the embodiments of the present disclosure.

Figure 14:
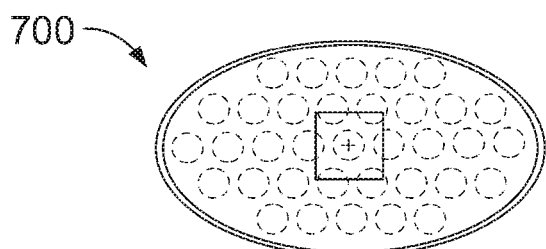
FIG. 14 illustrates a bottom view of an airflow-channeling surgical light system, according to an embodiment of the present disclosure.

FIG. 14 illustrates a bottom view of an airflow-channeling surgical light system 700, according to an embodiment of the present disclosure. As shown, the system 700 may be elliptical, instead of circular.

Figure 15:
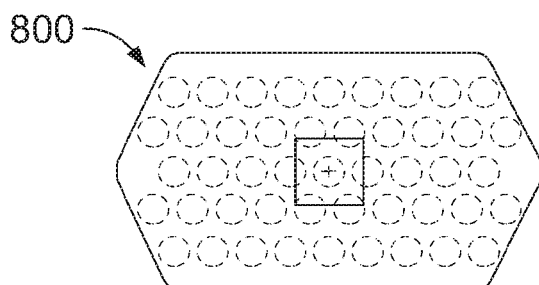
FIG. 15 illustrates a bottom view of an airflow-channeling surgical light system, according to an embodiment of the present disclosure.

FIG. 15 illustrates a bottom view of an airflow-channeling surgical light system 800, according to an embodiment of the present disclosure. As shown, the system 800 may include linear outer edges. In general, the light systems shown and described may be various shapes and sizes, such as square, rectangular, triangular, circular, elliptical, ovoid, irregularly-shaped, and/or the like. Additionally, the light systems may be configured with concentric rings with an air void between or around them.

Figure 16:
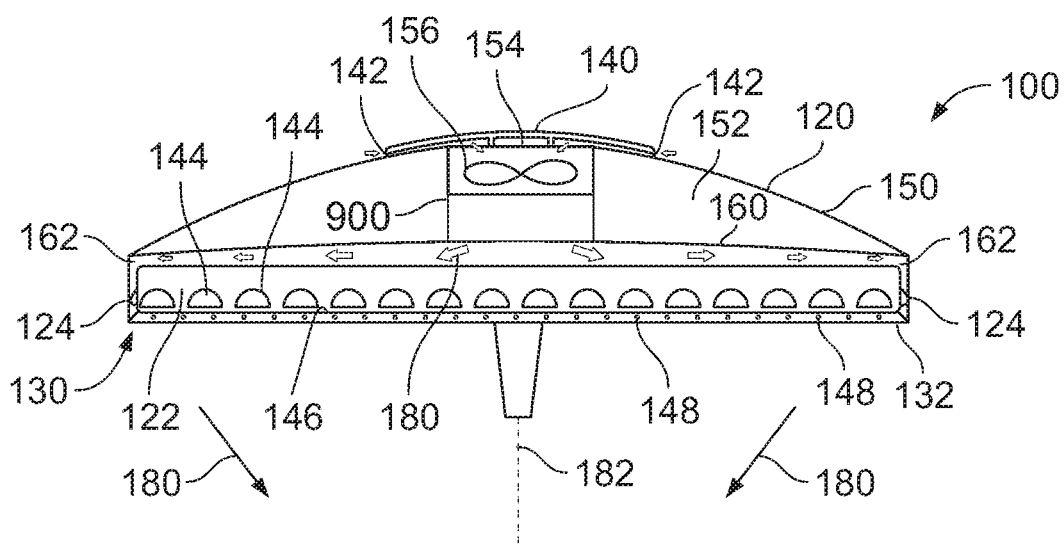
FIG. 16 illustrates a lateral internal view of an airflow-channeling surgical light system, according to another embodiment of the present disclosure.
Figure 17:
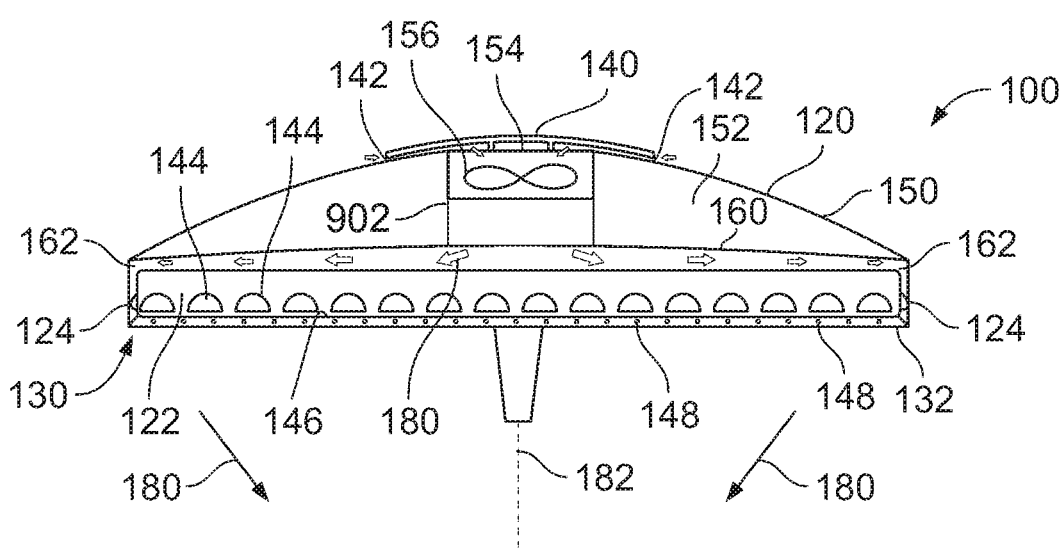
FIG. 17 illustrates a lateral internal view of an airflow-channeling surgical light system, according to another embodiment of the present disclosure.

Variations and modifications to the various embodiments are contemplated. For example, FIGS. 16 and 17 illustrate lateral internal views of the airflow-channeling surgical light system 100, according to other embodiments of the present disclosure. It should be noted that like numerals represent like parts in the various Figures. Similar to the embodiment illustrated in FIG. 6, in the embodiments illustrated in FIGS. 16 and 17, the main body 120 may include the outer shroud 150 that defines the internal chamber 152. The opening 154 is formed through the top of the outer shroud 150. The covering cap 140 is secured to the main body 120 within the opening 154 such that the air inlet passage 142 forms (or otherwise is) a gap between the lower surface of the covering cap 140 and the upper surface of the outer shroud 150.

The fan 156 (such as an electric, piezoelectric, or other such fan) is secured within the internal chamber 152 underneath the covering cap 140. Unlike the embodiment illustrated in FIG. 6, the embodiments illustrated in FIGS. 16 and 17 do not include the air filter 158 (e.g., a particulate arrestor), but instead include different air cleansing devices configured to sterilize or purify the air flow. However, it should be appreciated that although FIGS. 16 and 17 illustrate types of sterilizing and purifying devices, different types of sterilizing or purifying devices may be used. Additionally, different types of air filtering devices may be used instead of the illustrated air filter 158. In one or more embodiments, a device is positioned underneath the fan 156 in the air flow path thereof to at least one of filter, sterilize or purify the air flow generated by the fan 156. For example, the air cleansing device may be any type of mechanical or electrical air filtering device, air sterilizing device and/or air purifying device that is in the air flow path of the fan 156, which may, for example, remove particulates from the air flow, cleanse the air and/or deliver cleaning agents or chemicals in the air flow, among providing other air filtering, air sterilizing or air purifying arrangements.

More particularly, in the embodiment illustrated in FIG. 16, the air cleansing device is an air sterilizing device 900 that may be positioned underneath (or above) the fan 156 or may be in communication remotely to the surgical light system 100. The air sterilizing device 900 may be any type of device that effects a sterilization of the air flow from the fan 156, which may include introducing or adding a cleansing or sterilizing agent or chemical into the air flow path from the fan 156. Thus, the air sterilizing device 900 in various embodiments removes or changes the material properties of the contaminants or air particles to sterilize the air flow that is thereafter delivered as discussed herein. For example, the air sterilizing device 900 device may inject a cleansing or sterilizing agent or chemical into the air flow path that not only sterilizes or sanitizes the air, but also sterilizes or sanitizes the surfaces through which the air flows. It should be noted that any type of sterilizing or sanitizing method may be performed by the air sterilizing device 900, which in some embodiments may include using non-chemical methods to perform the sterilizing or sanitizing.

In the embodiment illustrated in FIG. 17, the air cleansing device is an air purifying device 902 that may be positioned underneath the fan 156. The air purifying device 902 may be any type of device that purifies the air flow from the fan 156. Thus, the air purifying device 902 in various embodiments changes the material properties of the contaminants or air particles to purify the air flow that is thereafter delivered as discussed herein. For example, the air purifying device 902 device may use one or more air ionization processes to purify the air flow, which can also effect a cleansing or purifying of the surfaces through which the air flows. It should be noted that any type of purifying method may be performed by the air purifying device 902, which in some embodiments may include using non-ionization methods to perform the sterilizing or sanitizing (e.g., different types of UV lights and catalysts).

It should be appreciated that any air purifying device may be used in or with one or more embodiments. For example, in one or more embodiments, any type of air purifying device that removes contaminants and sanitizes both the air and surfaces may be used. In some embodiments, the air purifying device 902 is any device used to kill, render impotent or reduce bacteria, viruses, mold, fungi, allergens, VOCs, etc. Some examples of the air purifying device 902 include, but are not limited to ultraviolet (UV) light, vaporized hydrogen peroxide (VHP), nano technology, ionization, bi-polar ionization, hydroxyl radicals, hydroperoxides, etc.

Additionally, it should also be appreciated that one or more air filtering, air sterilizing and/or air purifying devices or methods described herein may be used in combination with each other, for example, in a multi-stage cleaning design.

It should be noted that the other components of the airflow-channeling surgical light system 100 illustrated in FIGS. 16 and 17 are the same as the components described herein with respect to the airflow-channeling surgical light system 100 illustrated in FIG. 6 and will not be described again.

Figure 18:
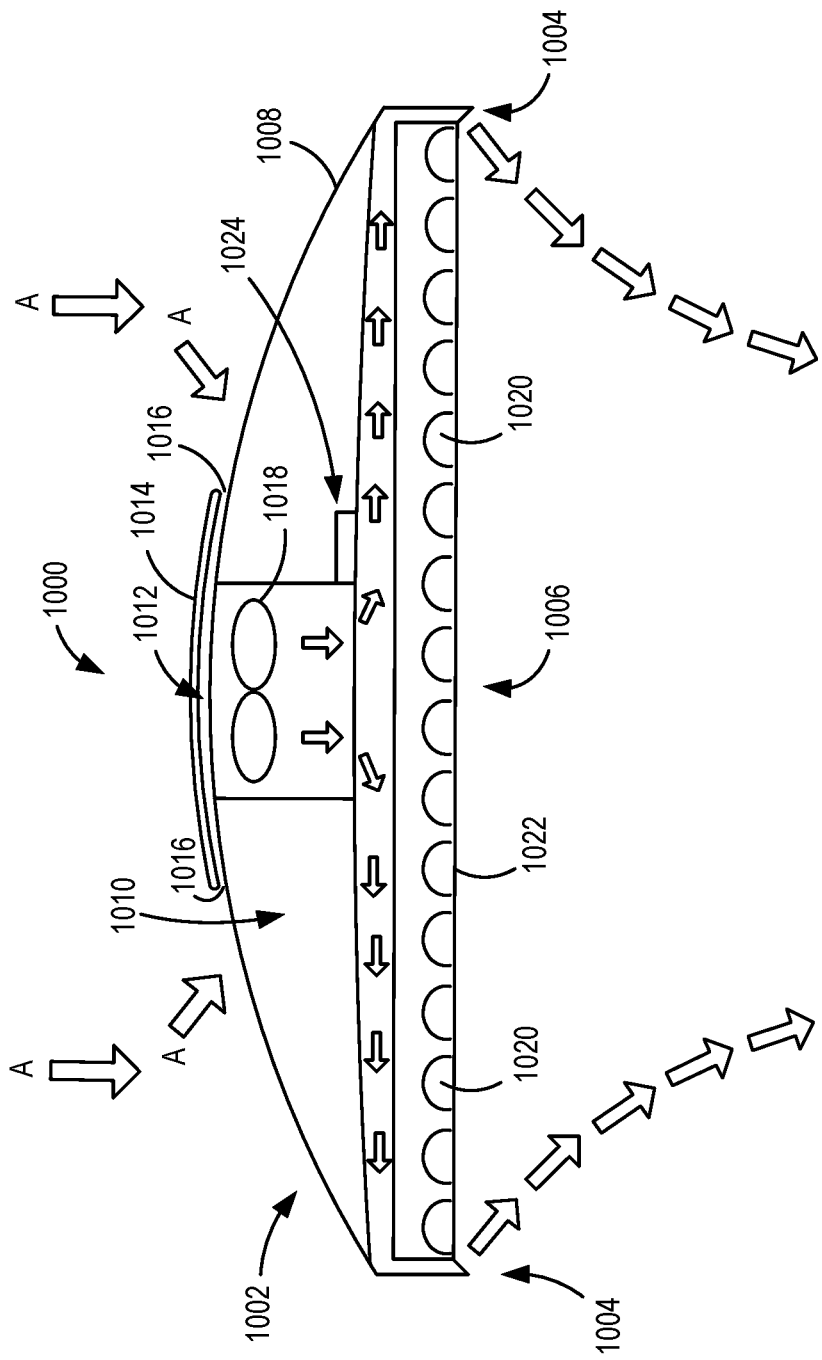
FIG. 18 illustrates a lateral internal view of an airflow-channeling surgical light system, according to an embodiment of the present disclosure.

In some embodiments, airflow speed and volume are controlled based on an angle (e.g., tilt) of a surgical light system 1000 as shown in FIGS. 18 and 19, such that the amount of air directed or forced around a periphery of a lighting assembly 1002 and out through airflow outlets 1004 formed around the periphery of the lighting assembly 1002 is controlled. That is, in some embodiments, the airflow caused to pass through the airflow outlets 1004 is changed based on an angle of the lighting assembly 1002, which may be detected in one or more directions or axes. It should be appreciated that the surgical light system 1000 includes similar components to the surgical light system 100 with the addition of airflow speed control features as described below. Thus, in some embodiments, the surgical light system 1000 is embodied as the surgical light system 100 with the airflow speed control features provided to control an amount of airflow out of the surgical light system 100 based on an angle of the surgical light system 100 relative to horizontal or vertical. Accordingly, various embodiments control the movement or flow of air that exits the surgical light system 100 or the surgical light system 1000.

As can be seen in FIGS. 18 and 19, the forced air is directed out from a lower side 1006 of the lighting assembly 1002. The delivery of the forced air from the lighting assembly 1002 generates a pressure zone underneath the lighting assembly 1002, which reduces air turbulence, which as described herein, reduces the possibility of contaminants passing onto or into the surgical site or back into the surgical light system 1000.

Similar to the embodiment illustrated in FIG. 6, in the embodiments illustrated in FIGS. 18 and 19, the lighting assembly 1002 defines a main body and includes an outer shroud 1008 that defines the internal chamber 1010. An opening 1012 is formed through the top of the outer shroud 1008. A covering cap 1014 is secured to the lighting assembly 1002 at or within the opening 1002 such that air inlet passages 1016 form (or otherwise are) a gap between the lower surface of the covering cap 1014 and the upper surface of the outer shroud 1008 to allow airflow from outside the lighting assembly 1002 into the lighting assembly 1002 as illustrated by the arrows A.

In the illustrated embodiment, a fan 1018 (such as an electric, piezoelectric, or other such fan) is coupled or secured within the internal chamber 1010 underneath the covering cap 1014. The fan 1018 operates as a local air source for the surgical light system 1000 that draws air into the lighting assembly 1002 and forces the air out through the airflow outlets 1004. As should be appreciated, different air sources can be provided. For example, instead of the local air source illustrated in FIG. 18, airflow can be delivered from a remote source, such as remote fan or system air source that is directed into the lighting assembly 1002. In this embodiment, the fan 1018 may be removed or turned off until additional flow of air is needed (e.g., a requirement for additional flow of air).

The surgical light system 1000, similar to the embodiment illustrated in FIG. 6, includes a plurality of light units 1020 above a lens or transparent panel 1020. The light units 1020 operate as otherwise described herein.

In the embodiments of FIGS. 18 and 19, the lighting assembly 1002 includes a tilt detection unit 1024, which is illustrated as mounted within the outer shroud 1008. However, it should be appreciated that the tilt detection unit 1024 can be mounted at different locations within, along or outside of the lighting assembly 1002 that allows for detection of a tilt or angle of the lighting assembly 1002 relative to a base plane (e.g., relative to horizontal or vertical). In some embodiments, the tilt detection unit 1024 is mounted along a flat or horizontal surface of the lighting assembly 1002, such as positioned to extend along a horizontal axis of the lighting assembly 1002 when the lighting assembly 1002 is directed downwards. However, other angled positions are contemplated by the present disclosure.

In various embodiments, the tilt detection unit 1024 is configured to determine the angle or pitch of the lighting assembly 1002 relative to horizontal or vertical. In one example, the tilt detection unit 1024 is a three-axis accelerometer capable of detecting and outputting a tilt angle of the lighting assembly 1002. In another example, the tilt detection unit 1024 is a mechanical level or electronic level capable of detecting a tilt angle. It should be noted that any suitable tilt angle measuring or detecting device can be used.

In one embodiment, the tilt detection unit 1024 is configured to generate an output signal representative of a tilt angle of the lighting assembly 1002. For example, the tilt detection unit 1024 outputs an angle of tilt of the lighting assembly 1002 relative to horizontal (e.g., zero degrees at horizontal). Thus, in various embodiments, the tilt detection unit 1024 is a device or module configured to detect and output current tilt angle information, which is representative of a tilt of the lighting assembly 1002. In one embodiment, as illustrated in FIG. 20, the tilt detection unit 1024 generates a control signal output to a controller 1026 that controls a speed of the fan 1018, thereby controlling the airflow speed from the lighting assembly 1002. It should be appreciated that that controller 1026 forms part of the fan 1018 in some embodiments, but may be a separate control unit in other embodiments. The controller 1026 can be any suitable mechanism for controlling the speed of the fan blades in some embodiments, such as a potentiometer for a DC controlled fan arrangement.

Additionally, in some embodiments, the controller 1026 is operable to control an airflow control mechanism that forms part of or is coupled to the fan 1018 or to a remote air delivery device. For example, in some embodiments, mechanical airflow restrictors 1028 are provided and controlled by the controller 1026. In one embodiment, the airflow restrictors 1028 are louvers that mechanically adjust to change the airflow exiting from the fan 1018 or remote air delivery device (e.g., restrict or change the direction of airflow by changing an angle of the slats for the louvers based on the tilt angle of the lighting assembly 1002)

Thus, in response to a change in the tilt angle of the lighting assembly 1002, in some embodiments, a control signal is generated that causes the speed of the fan 1018 to change (e.g., causes the fan to increase or decrease an airflow speed generated by the fan 1018). For example, when the lighting assembly 1002 is tilted, such as by moving or tilting a boom art to which the lighting assembly 1002 is attached (as described herein), the tilt detection unit 1024 generates a control signal to change the airflow speed for the fan 1018.

In one embodiment, the tilt control unit includes a processor 1030 and a memory 1032. The processor 1030 in one example accesses one or more tables in the memory 1032 to determine the control signal to generate based on a current tilt angle of the lighting assembly 1002. It should be noted that in some embodiments, a control signal is not generated until a predefined time period after the tilting of the lighting assembly 1002 has stopped (e.g., five seconds). However, in other embodiments, the control signals are generated continuously as the lighting assembly 1002 is tilted.

The processor 1030 in some embodiments controls the operation of the tilt generation unit 1024 to acquire and process sensed or measured tilt angle information to generate control signals for the controller 1026. Thus, the processor 1030 is configured in various embodiments to process received information to generate a control signal for controlling the airflow speed or velocity of the fan 1018.

In one embodiment, the processor 1030 accesses one or more tables in the memory 1032 to generate the control signal. For example, based on the type of the fan 1018 and/or the type of the lighting assembly 1002, a specific table is accessed to determine the appropriate control signal to generate in order to achieve a desired or required airflow output from the fan 1018 (e.g., based on a desired or required reduced turbulence airflow under the lighting assembly 1002 or to maintain a constant pressure thereunder).

The memory 1032 in some embodiments includes programming or instructions for controlling the processor 1030 to perform one or more operations herein to thereby transform the processor 1030 into a specialized processor. Additionally, the processor 1030 may be configured to control the tilt angle detection unit 1024 to provide, automatic, semi-automatic or manual control and operation.

It should be noted that the memory 1032, which may be any type of electronic storage device, can be coupled to the processor 1030 (or form part of the processor 1030). The processor 1030, thus, may access the memory 1032 to obtain stored information as described herein, such as the tables 1100 illustrated in FIG. 21. The tables 1100, illustrated as Tables 1-3, correspond to different types of fans 1018 in one embodiment and are used to generate the control signals to achieve the desired or required airflow (e.g., change in power supplied to the fan 1018 for each different angle). However, in some embodiments, the Tables 1-3 can optionally or additionally relate to other control factors, such as the type of lighting assembly 1002, the dimensions of the room in which the lighting assembly 1002 is located, etc.

The tables 1100 define control parameters or characteristics for generating control signals. For example, based on a calculated or detected angle of the lighting assembly 1002, the tables 1100 define airflow control parameters (e.g., fan speed or fan power) to adjust the airflow speed or velocity of the fan 1018, which may be controlled in different ways as described herein. The airflow control parameters can be based on, for example, empirical test data, ideal control requirements, etc. The tables 1100 in some embodiments define presets or predetermined values to control the airflow.

Thus, as the lighting assembly 1002 is tilted, such as illustrated in FIG. 19, the fan 1018 is controlled to adjust an airflow speed from the lighting assembly 1002. As shown in FIG. 19, which is merely an example for illustration, when the lighting assembly 1002 is horizontal (at a horizontal position or orientation 1050), airflow from the lighting assembly 1002 is controlled to be 100% flow. It should be noted that 100% flow can be 100% or the highest operating speed of the fan 1018 or can be a maximum airflow for a particular or desired environment or setting, which may be less than 100% speed for the fan 1018. As can also be seen, in the illustrated example, when the lighting assembly 1002 is vertical, a significantly reduced airflow is provided, illustrated as a 5% airflow. As should be appreciated, this airflow at the vertical orientation or position 1070 is a minimum airflow, which may be other values, such as 1%, 10%, 12%, or any other value.

In an intermediate position 1060, illustrated as approximately halfway between horizontal and vertical, the airflow from the lighting assembly 1002 is controlled to be a 50% flow. Again, the airflow percentage value is shown merely for illustration and different airflow values can be provided at the different positions, including at position between 1050 and 1060, and 1060 and 1070. Additionally, it should be appreciated that the airflow values in some embodiments change linearly as the lighting assembly 1002 is tilted, while in other embodiments, the airflow values change non-linearly. The airflow values in some embodiments are based on desired or required airflow amounts under the lighting assembly 1002.

Thus, various embodiments control the airflow speed or velocity from a lighting assembly, such as a surgical lighting assembly, based on a tilt angle of the lighting assembly. For example, in some embodiments, because the system has more surface area in the horizontal position than in the vertical position, the horizontal position will block more air than the vertical. With the present disclosure, to maintain a desired airflow adjacent to an underside of the lighting assembly, various embodiments slow down the air to keep the pressure under the lighting assembly constant as the lighting assembly is moved from the horizontal position to the vertical position, and at positions therebetween. Various embodiments provide an automatic adjustment of the airflow depending on the angle at which the lighting assembly is placed. For example, as described herein, an accelerometer or mechanical level detection device sends one or more signals to motor or air delivery source. In some embodiments, air delivery is reduced according to the signal that is sent as the lighting assembly is rotated from horizontal.

It should be noted that the various embodiments may be implemented in hardware, software or a combination thereof. The various embodiments and/or components, for example, the modules, or components and controllers therein, also may be implemented as part of one or more computers or processors or field-programmable gate arrays (FPGAs). The computer or processor or FPGA may include a computing device, an input device, a display unit and an interface, for example, for accessing the Internet. The computer or processor may include a microprocessor. The microprocessor may be connected to a communication bus. The computer or processor may utilize external communications such as RS-232, Bluetooth, USB, or Ethernet, among others. The computer or processor or FPGA may also include a memory. The memory may include Random Access Memory (RAM) and Read Only Memory (ROM). The computer or processor or FPGA further may include a storage device, which may be a hard disk drive or a removable storage drive such as a floppy disk drive, optical disk drive, and the like. The storage device may also be other similar means for loading computer programs or other instructions into the computer or processor.

As used herein, the terms "system," "circuit," "component," or "module" may include a hardware and/or software system that operates to perform one or more functions. For example, a module, circuit, component, or system may include a computer processor, controller, or other logic-based device that performs operations based on instructions stored on a tangible and non-transitory computer readable storage medium or computer storage media, such as a computer memory. Alternatively, a module, circuit, component, or system may include a hard-wired device that performs operations based on hard-wired logic of the device. The modules or circuits or components shown in the attached figures may represent the hardware that operates based on software or hard-wired instructions, the software that directs hardware to perform the operations, or a combination thereof.

The block diagrams of embodiments herein illustrate various blocks labeled "circuit" or "module." It is to be understood that the circuits or modules may be implemented as hardware with associated instructions (e.g., software stored on a tangible and non-transitory computer readable storage medium, such as a computer hard drive, ROM, RAM, or the like) that perform the operations described herein. The hardware may include state machine circuitry hard-wired to perform the functions described herein. Optionally, the hardware may include electronic circuits that include and/or are connected to one or more logic-based devices, such as microprocessors, processors, controllers, or the like. Optionally, the modules may represent processing circuitry such as one or more field programmable gate array (FPGA), application specific integrated circuit (ASIC), or microprocessor. The circuit modules in various embodiments may be configured to execute one or more algorithms to perform functions described herein. The one or more algorithms may include aspects of embodiments disclosed herein, whether or not expressly identified in a flowchart or a method.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

While various spatial and directional terms, such as top, bottom, lower, mid, lateral, horizontal, vertical, front and the like may be used to describe embodiments of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A light system comprising:
   a main body defining an internal chamber,
   a lighting assembly secured to the main body, wherein the lighting assembly comprises at least one light unit configured to emit light;
   a fan configured to generate an airflow;
   an airflow circuit configured to direct the airflow out of the main body of the lighting assembly; and
   a tilt detection unit configured to detect a tilt angle of the lighting assembly and to generate a control signal to cause a speed of the airflow generated by the fan to change based at least on a detected change in the tilt angle of the lighting assembly, wherein the control signal is generated to decrease the speed of the airflow as the tilt angle of the lighting assembly indicates tilt of the lighting assembly having an increased position of the main body toward vertical such that light emitted from the lighting assembly is directed more horizontally.

2. The light system of claim 1, wherein the tilt detection unit is configured to generate the control signal to cause a speed of the fan to change.

3. The light system of claim 1, further comprising an airflow restrictor coupled to the fan, and wherein the tilt detection unit is configured to generate the control signal to cause the airflow restrictor to change an amount of air flowing from the fan.

4. The light system of claim 1, wherein the tilt detection unit comprises one or more accelerometers.

5. The light system of claim 1, wherein the tilt detection unit is configured to generate the control signal to cause a maximum airflow at a horizontal position of the lighting assembly and a minimum airflow at a vertical position of the lighting assembly.

6. The light system of claim 1, wherein the fan is positioned within the lighting assembly to define a local air source.

7. The light system of claim 1, wherein in a horizontal position of the main body light is emitted by the lighting assembly in a vertical direction and in vertical position of the main body light is emitted by the lighting assembly in a horizontal direction.

8. The light system of claim 1, wherein the airflow circuit extends around a periphery of the lighting assembly, and the airflow circuit is configured to direct airflow out of the main body underneath the lighting assembly, wherein the speed of the airflow is maintained at a desired airflow out of the main body to keep a constant air pressure under the lighting assembly.

9. A method for controlling airflow from a lighting assembly, the method comprising:
   detecting a tilt angle of a lighting assembly, the lighting assembly comprising at least one light unit configured to emit light and an airflow circuit configured to direct the airflow from a fan out of the main body of the lighting assembly; and
   generating a control signal to cause a speed of airflow generated by the fan to change based at least on the detected change in the tilt angle of the lighting assembly, wherein the control signal is generated to decrease the seed of the airflow as the tilt angle of the lighting assembly indicates tilt of the lighting assembly having an increased position of the main body toward vertical such that light emitted from the lighting assembly is directed more horizontally.

10. The method of claim 9, further comprising generating the control signal to cause a speed of the fan to change.

11. The method of claim 9, wherein the lighting assembly further comprises an airflow restrictor coupled to the fan, and further comprising generating the control signal to cause the airflow restrictor to change an amount of air flowing from the fan.

12. The method of claim 9, further comprising detecting the tilt angle of the lighting assembly using one or more accelerometers.

13. The method of claim 9, further comprising generating the control signal to cause a maximum airflow at a horizontal position of the lighting assembly and a minimum airflow at a vertical position of the lighting assembly.

14. The method of claim 9, wherein the fan is positioned within the lighting assembly to define a local air source.

15. The method of claim 9, wherein in a horizontal position of the main body light is emitted by the lighting assembly in a vertical direction and in vertical position of the main body light is emitted by the lighting assembly in a horizontal direction.

16. The method of claim 9, wherein the airflow circuit extends around a periphery of the lighting assembly, and the airflow circuit is configured to direct airflow out of the main body underneath the lighting assembly.

17. One or more computer storage media having computer-executable instructions for controlling airflow from a lighting assembly that, upon execution by a processor, cause the processor to at least:
   detect a tilt angle of a lighting assembly, the lighting assembly comprising at least one light unit configured to emit light and an airflow circuit configured to direct the airflow from a fan out of the main body of the lighting assembly; and
   generate a control signal to cause a speed of airflow generated by the fan to change based at least on the detected change in the tilt angle of the lighting assembly, wherein the control signal is generated to decrease the speed of the airflow as the tilt angle of the lighting assembly indicates tilt of the lighting assembly having an increased position of the main body toward vertical such that light emitted from the lighting assembly is directed more horizontally.

18. The one or more computer storage media of claim 17 having further computer-executable instructions that, upon execution by a processor, cause the processor to at least:
   generate the control signal to cause a speed of the fan to change.

19. The one or more computer storage media of claim 17, wherein the lighting assembly further comprises an airflow restrictor coupled to the fan, the one or more computer storage media having further computer-executable instructions that, upon execution by a processor, cause the processor to at least:
   generate the control signal to cause the airflow restrictor to change an amount of air flowing from the fan.

20. The one or more computer storage media of claim 17 having further computer-executable instructions that, upon execution by a processor, cause the processor to at least:
   generate the control signal to cause a maximum airflow at a horizontal position of the lighting assembly and a minimum airflow at a vertical position of the lighting assembly.

* * * * *